US012702447B2

(12) United States Patent
Oikawa et al.

(10) Patent No.: US 12,702,447 B2
(45) **Date of Patent: *Aug. 11, 2026**

(54) ROD FOR SPINAL FIXTURE, AND SPINAL FIXTURE COMPRISING SAME

(71) Applicant: GLOBERIDE, Inc., Tokyo (JP)

(72) Inventors: Katsuhiro Oikawa, Tokyo (JP); Takuji Kawamura, Tokyo (JP)

(73) Assignee: GLOBERIDE, INC, Tokyo (JP)

(*) Notice: Subject to any disclaimer, the term of this patent is extended or adjusted under 35 U.S.C. 154(b) by 195 days.

This patent is subject to a terminal disclaimer.

(21) Appl. No.: 18/269,488

(22) PCT Filed: Oct. 12, 2021

(86) PCT No.: PCT/JP2021/037720

§ 371 (c)(1), (2) Date: Jun. 23, 2023

(87) PCT Pub. No.: WO2022/149326

PCT Pub. Date: Jul. 14, 2022

(65) Prior Publication Data

US 2024/0058038 A1 Feb. 22, 2024

(30) Foreign Application Priority Data

Jan. 5, 2021 (JP) ................................ 2021-000613

(51) Int. Cl.
*A61B 17/70* (2006.01)
*A61L 31/12* (2006.01)
(Continued)

(52) U.S. Cl.
CPC ...... *A61B 17/7002* (2013.01); *A61B 17/7004* (2013.01); *A61L 31/128* (2013.01);
(Continued)

(58) Field of Classification Search
CPC .................................. A61B 17/7002–17/7013
See application file for complete search history.

(56) References Cited

U.S. PATENT DOCUMENTS 5,415,661 A * 5/1995 Holmes ............. A61B 17/7031 606/255
5,556,687 A 9/1996 McMillin
(Continued)

FOREIGN PATENT DOCUMENTS

DE 102013013024 A1 * 2/2014 ......... A61B 17/7004
EP 2 389 124 11/2011
(Continued)

OTHER PUBLICATIONS

Jul. 2, 2024 Extended European Search Report issued in European Patent Application No. 21917551.0.
(Continued)

*Primary Examiner* — Julianna N Harvey
(74) *Attorney, Agent, or Firm* — Oliff PLC

(57) ABSTRACT

Provided is a fixture rod having improved bonding strength between a core member and a reinforcing fiber layer, high rigidity, and high durability against a deformation load. The fixture rod according to one embodiment of the present disclosure comprises: a core member containing fibers; and a reinforcing fiber layer provided on the core member, and a part of the fibers of the core member is exposed from the core member, and a part of the fibers with the exposed part is embedded in the reinforcing fiber layer.

11 Claims, 8 Drawing Sheets

(51) Int. Cl.
*A61L 31/14* (2006.01)
*B29C 70/08* (2006.01)
*B29C 70/30* (2006.01)
*B29L 31/00* (2006.01)

(52) U.S. Cl.
CPC ........... *A61L 31/143* (2013.01); *B29C 70/081* (2013.01); *B29C 70/30* (2013.01); *B29K 2995/0082* (2013.01); *B29L 2031/7546* (2013.01)

(56) References Cited

U.S. PATENT DOCUMENTS

| | | | | |
|---|---|---|---|---|
| 2004/0049189 | A1* | 3/2004 | Le Couedic | A61B 17/7031 606/907 |
| 2004/0215191 | A1* | 10/2004 | Kitchen | A61B 17/7029 606/264 |
| 2006/0189982 | A1* | 8/2006 | Lange | A61B 17/701 606/301 |
| 2006/0247638 | A1 | 11/2006 | Trieu et al. | |
| 2006/0276788 | A1* | 12/2006 | Berry | A61B 17/7005 606/301 |
| 2007/0233073 | A1* | 10/2007 | Wisnewski | A61B 17/7019 606/250 |
| 2008/0177317 | A1* | 7/2008 | Jackson | A61B 17/7026 606/301 |
| 2008/0234744 | A1* | 9/2008 | Zylber | A61B 17/7022 606/264 |
| 2008/0262548 | A1 | 10/2008 | Lange et al. | |
| 2009/0018583 | A1* | 1/2009 | Song | A61B 17/705 606/264 |
| 2009/0093819 | A1 | 4/2009 | Joshi | |
| 2009/0112265 | A1* | 4/2009 | Hudgins | A61B 17/7031 606/301 |
| 2009/0118831 | A1 | 5/2009 | Trieu | |
| 2009/0163955 | A1* | 6/2009 | Moumene | A61B 17/701 606/257 |
| 2009/0281573 | A1* | 11/2009 | Biedermann | A61B 17/7029 606/264 |
| 2009/0287251 | A1* | 11/2009 | Bae | A61B 17/7031 606/264 |
| 2010/0137912 | A1* | 6/2010 | Alcock | A61B 17/7022 606/264 |
| 2011/0060365 | A1 | 3/2011 | Felix et al. | |
| 2011/0071570 | A1 | 3/2011 | Trieu | |
| 2011/0106162 | A1* | 5/2011 | Ballard | A61B 17/701 606/279 |
| 2011/0152937 | A1 | 6/2011 | Trieu | |
| 2011/0282395 | A1 | 11/2011 | Beyar et al. | |
| 2011/0307014 | A1 | 12/2011 | Niinomi et al. | |
| 2012/0029564 | A1 | 2/2012 | Trieu et al. | |
| 2012/0071928 | A1* | 3/2012 | Jackson | A61B 17/7008 606/257 |
| 2012/0196068 | A1 | 8/2012 | Gong et al. | |
| 2013/0204368 | A1 | 8/2013 | Prevost | |
| 2013/0213535 | A1 | 8/2013 | Niinomi et al. | |
| 2015/0209095 | A1* | 7/2015 | Lu | A61L 31/028 424/602 |
| 2016/0303824 | A1* | 10/2016 | Takebe | B29C 70/0035 |
| 2017/0042593 | A1 | 2/2017 | Newman et al. | |
| 2024/0081867 | A1 | 3/2024 | Oikawa et al. | |

FOREIGN PATENT DOCUMENTS

| | | | |
|---|---|---|---|
| EP | 2 982 504 | A1 | 2/2016 |
| EP | 3236866 | A1 | 11/2017 |
| GB | 2256615 | A | 12/1992 |
| JP | H04-366616 | A | 12/1992 |
| JP | H11-296033 | A | 10/1999 |
| JP | H11-347047 | A | 12/1999 |
| JP | 2011508623 | A | 3/2011 |
| JP | 2011-256443 | A | 12/2011 |
| JP | 2015-186641 | A | 10/2015 |
| JP | 2020-137454 | A | 9/2020 |
| KR | 102187523 | B1 | 12/2020 |
| WO | 2006/044315 | A2 | 4/2006 |
| WO | 2007/097905 | A2 | 8/2007 |
| WO | 2011/042998 | A1 | 4/2011 |
| WO | 2014162873 | A1 | 10/2014 |

OTHER PUBLICATIONS

Dec. 5, 2023 Office Action issued in Japanese Patent Application No. 2021-000613.

International Preliminary Report on Patentability for related International Application No. PCT/JP2021/037720; action dated Jul. 4, 2023; (12 pages).

International Search Report for related International Application No. PCT/JP2021/037720; action dated Jul. 14, 2022; (3 pages).

Written Opinion for related International Application No. PCT/JP2021/037720; action dated Jul. 14, 2022; (5 pages).

Jul. 15, 2025 Office Action issued in Korean Patent Application No. 10-2023-7028508.

Dec. 5, 2023 Office Action issued in Japanese Patent Application No. 2021-009692.

Jul. 31, 2024 Extended European Search Report issued in European Patent Application No. 21921161.2.

Jul. 28, 2022 International Search Report issued in International Patent Application No. PCT/JP2021/037721.

Jul. 28, 2022 Written Opinion issued in International Patent Application No. PCT/JP2021/037721.

Jul. 20, 2023 International Preliminary Report on Patentability issued in International Patent Application No. PCT/JP2021/037721.

Apr. 11, 2025 Office Action issued in U.S. Appl. No. 18/272,981.

May 20, 2025 Office Action issued in Korean Patent Application No. 10-2023-7023502.

Aug. 11, 2025 Office Action issued in U.S. Appl. No. 18/027,818.

Feb. 28, 2025 Office Action issued in U.S. Appl. No. 18/027,818.

Jun. 19, 2025 Office Action issued in Chinese Patent Application No. 202180053600.2.

Feb. 19, 2025 Office Action issued in Korean Patent Application No. 10-2023-7006589.

Dec. 11, 2024 Office Action issued in Chinese Patent Application No. 202180053600.2.

Apr. 26, 2024 Search Report issued in European Patent Application No. 21875136.0.

Nov. 21, 2023 Office Action issued in Japanese Patent Application No. 2020-163964.

Olffice Action for related Japanese Application No. 2020-163964; action dated Jun. 27, 2023; (7 pages).

Preliminary Report on Patentability for related International Application No. PCT/JP2021/033268; action dated Mar. 28, 2023; (9 pages).

International Search Report for related International Application No. PCT/JP2021/033268; action dated Apr. 7, 2022; 5 pages).

Written Opinion for related International Application No. PCT/JP2021/033268; action dated Apr. 7, 2022; (4 pages).

Sep. 27, 2025 Office Action issued in Chinese Patent Application No. 202180088813.9.

Aug. 11, 2025 Office Action issued in U.S. Appl. No. 18/272,981.

Feb. 7, 2026 Office Action issued in Chinese Patent Application No. 202180088813.9.

Dec. 25, 2026 Office Action issued in Chinese Patent Application No. 202180091658.6.

Feb. 5, 2026 Office Action issued in U.S. Appl. No. 18/272,981.

Jun. 9, 2026 Notice of Allowance issued in U.S. Appl. No. 18/272,981.

May 10, 2026 Office Action issued in Chinese Patent Application No. 202180091658.6.

May 29, 2026 Office Action issued in Korean Patent Application No. 10-2023-7028508.

Jun. 24, 2026 Office Action issued in Chinese Patent Application No. 202180088813.9.

* cited by examiner

ROD FOR SPINAL FIXTURE, AND SPINAL FIXTURE COMPRISING SAME

CROSS-REFERENCE TO RELATED APPLICATIONS

The present application is a National Stage of International Application No. PCT/JP2021/037720 filed on Oct. 12, 2021 which claims priority to and the benefit of Japanese Patent Application No. 2021-000613 filed on Jan. 5, 2021, the contents of which are incorporated herein by reference in their entirety.

FIELD

The present disclosure relates to a fixture rod used for a fixture configured to fix a spine and a spinal fixture comprising the same.

BACKGROUND

Conventionally, a fixture rod using metal as a fixture for fixing the spine has been known.

Further, as such a fixture rod, for example, Patent Literature 1 discloses a spinal pedicle rod including an internally reinforced polymer core at least partially encased in a polymer coating.

CITATION LIST

Patent Literature

Patent Literature 1: Japanese Translation of PCT International Application Publication No. 2011-508623

SUMMARY

A fixture rod using metal is generally excellent in fixing force and strength, but has a problem that a magnetic field is affected by magnetization of the metal in the magnetic field at the time of imaging by MRI or the like, image disturbance occurs, and diagnosis based on a captured image is difficult. On the other hand, the rod disclosed in Patent Literature 1 does not have such a problem, but has a problem that it is difficult to reliably achieve uniform bonding even if an adhesive is used for bonding between a polymer core member and a covering layer thereof, and it is difficult to obtain stable bonding strength.

An object of the present disclosure is to provide a fixture rod having significantly improved bonding force between a core member and a reinforcing fiber layer, high rigidity, and high durability against a deformation load and a spinal fixture comprising the same. Purposes of the present disclosure other than this object will be clarified by referring to the overall description disclosed herein.

The fixture rod according to one embodiment of the present disclosure comprises: a core member containing fibers; and a reinforcing fiber layer provided on the core member, and a part of the fibers of the core member is exposed from the core member, and a part of the fibers with the exposed part is embedded in the reinforcing fiber layer.

In the fixture rod according to one embodiment of the present disclosure, the fiber of the core member is a long fiber.

In the fixture rod according to one embodiment of the present disclosure, the fibers of the core member are short fibers.

In the fixture rod according to one embodiment of the present disclosure, the fibers of the core member comprise a long fiber and a short fiber.

In the fixture rod according to one embodiment of the present disclosure, the fiber of the core member is configured such that an end portion as viewed in its longitudinal direction is exposed from the core member.

In the fixture rod according to one embodiment of the present disclosure, the fiber of the core member is configured such that an end portion as viewed in its radial direction is exposed from the core member.

In the fixture rod according to one embodiment of the present disclosure, the fiber of the core member is carbon, glass, aramid, boron, or SiC.

In the fixture rod according to one embodiment of the present disclosure, one recess or a plurality of recesses are formed on an outer surface of the core member.

In the fixture rod according to one embodiment of the present disclosure, the recess is formed in a circumferential direction of the core member.

In the fixture rod according to one embodiment of the present disclosure, the recess is formed in an axial direction of the core member.

In the fixture rod according to one embodiment of the present disclosure, the recess is formed in a direction inclined with respect to a circumferential direction of the core member.

The fixture rod according to one embodiment of the present disclosure is configured such that the recesses comprise two or more recesses formed in different directions.

The fixture rod according to one embodiment of the present disclosure is configured such that a depth of the recess is in a range of 3 μm to 200 μm.

The fixture rod according to one embodiment of the present disclosure is configured such that the core member contains a resin, and the resin is any of epoxy, phenol, unsaturated polyester, PA, PC, PPSU, POM, PP, PE, ABS, PS, PAEK, or PEEK.

A spinal fixture according to one embodiment of the present disclosure comprises any of the fixture rods described above.

According to each of the above embodiments of the present disclosure, it is possible to provide the fixture rod having high rigidity and high durability against the deformation load, in which the bonding force between the core member and the reinforcing fiber layer is significantly improved, and the spinal fixture comprising the same.

DETAILED DESCRIPTION

Hereinafter, an embodiment of a fixture rod according to the present disclosure will be specifically described with reference to the accompanying drawings. Components common in a plurality of drawings are assigned with the same reference signs throughout the plurality of drawings. It should be noted that each of the drawings is not always illustrated in a precise aspect ratio for the convenience of description.

Figure 1:
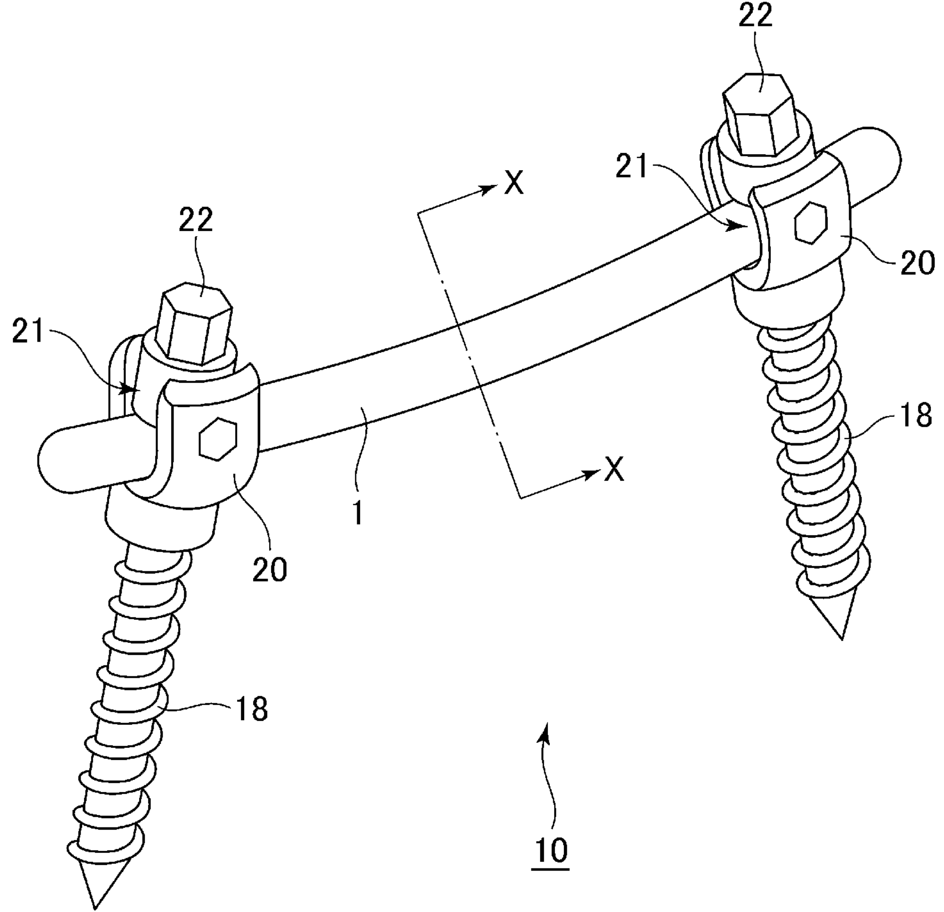
FIG. 1 is a view illustrating a spinal fixture 10 comprising a fixture rod according to one embodiment of the present disclosure.

FIG. 1 is a view illustrating a spinal fixture 10 comprising a fixture rod 1 according to one embodiment of the present disclosure. As illustrated in the drawing, the spinal fixture 10 comprises a plurality of screw members 18 (two screw members 18 in the example illustrated in the drawing) to be fixed to the bone of the spine, a plurality of rod fixing members 20 (two rod fixing members 20 in the example illustrated in the drawing) attached to the screw members 18 and each comprising a recess 21 for receiving the fixture rod and a pressing member 22, and the fixture rod 1 inserted into the recess 21 of the plurality of rod fixing members 20 and fixed by the pressing member 22.

Figure 2:
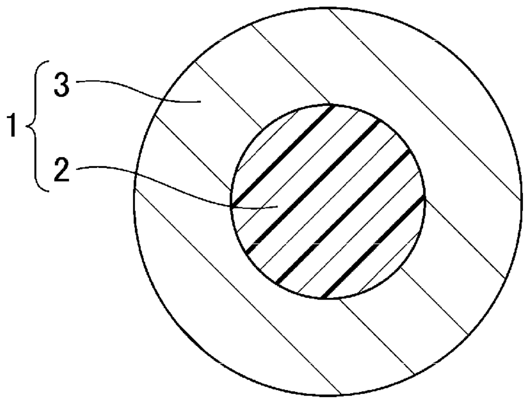
FIG. 2 is a view schematically illustrating a cross section of the fixture rod according to one embodiment of the present disclosure taken along a plane perpendicular to a central axis thereof.

Next, a layer structure of the fixture rod 1 according to one embodiment of the present disclosure used for the spinal fixture 10 will be described with reference to FIG. 2. FIG. 2 illustrates the fixture rod 1 illustrated in FIG. 1 as viewed in X-X section illustrated in the same drawing.

As illustrated in the drawing, the fixture rod 1 according to one embodiment of the present disclosure comprises a core member 2 containing fibers 4 and a reinforcing fiber layer 3 provided on the core member. A part of the fibers 4 of the core member is exposed from the core member 2, and a part of the fibers 4 with the exposed part is embedded in the reinforcing fiber layer 3. Here, the core member 2 contains the fiber 4, and thus, it is possible to increase bending rigidity and strength of the core member. The fiber 4 of the core member will be described more specifically below.

With the fixture rod 1 according to one embodiment of the present disclosure, it is possible to provide the fixture rod having a significantly improved bonding force between the core member and the reinforcing fiber layer, high rigidity, and high durability against a deformation load. More specifically, as the fiber 4 of the core member is exposed and inserted into the reinforcing fiber layer, bonding between the core member and the reinforcing fiber layer is strengthened. Further, a solid double structure is adopted, and a material having a large average bending elastic modulus is used for an outer layer as will be described later, and thus, it is possible to provide the fixture rod having excellent bending rigidity and crushing strength of the entire rod. Here, the average bending elastic modulus refers to a value calculated by dividing the bending rigidity of the entire corresponding portion by a second moment of the corresponding portion.

Here, in the fixture rod 1 according to one embodiment of the present disclosure, the core member 2 can be formed using a resin containing the fibers 4, and is configured such that the fibers 4 of the core member are short fibers. Since fiber directions can be randomly oriented when the short fibers are used in this manner, reinforcement in all directions is possible.

Further, in the fixture rod 1 according to one embodiment of the present disclosure, the core member 2 can be formed using a resin containing the fibers 4, and is configured such that the fibers of the core member are long fibers. As a result, the bending rigidity can be effectively improved.

Figure 3A:
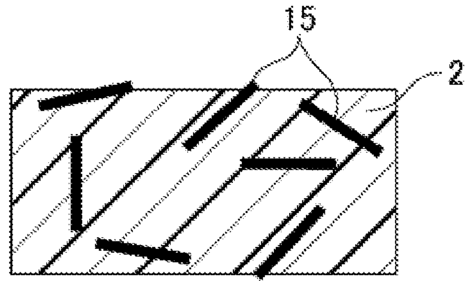
FIG. 3A is a view for describing a core member of the fixture rod according to one embodiment of the present disclosure.
Figure 3B:
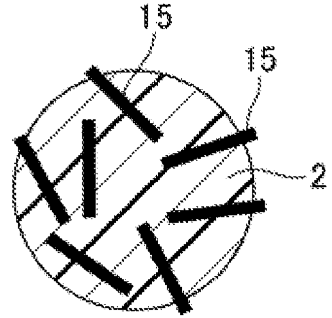
FIG. 3*b* is a view for describing a core member of the fixture rod according to one embodiment of the present invention.

Next, the core member 2 of the fixture rod 1 according to one embodiment of the present disclosure will be described with reference to FIG. 3. As illustrated in the drawing, in the fixture rod 1 according to one embodiment of the present disclosure, the fibers 4 of the core member 2 are short fibers 15, and partially exposed from the surface of the core member. In the example illustrated in the drawing, the short fibers 15 of the core member 2 are configured such that end portions (1 to 10 μm) thereof as viewed in its longitudinal direction are exposed from the core member 2. When the short fibers 15 are exposed in this manner, minute irregularities are generated on the surface of the core member 2, so that displacement between the core member 2 and the reinforcing fiber layer 3 can be suppressed.

Figure 4A:
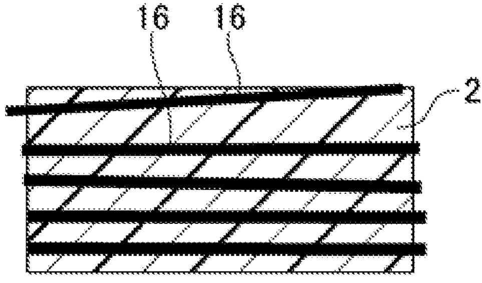
FIG. 4A is a view for describing a core member of the fixture rod according to one embodiment of the present disclosure.
Figure 4B:
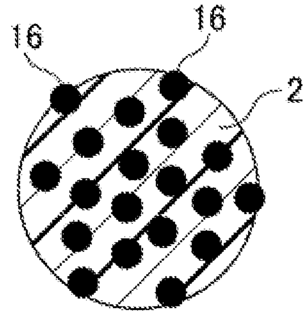
FIG. 4*b* is a view for describing a core member of the fixture rod according to one embodiment of the present invention.

Next, the core member 2 of the fixture rod 1 according to one embodiment of the present disclosure will be described with reference to FIG. 4. As illustrated in the drawing, in the fixture rod 1 according to one embodiment of the present disclosure, the fibers 4 of the core member 2 are long fibers 16, and partially exposed from the surface of the core member. In the example illustrated in the drawing, the short fibers 15 of the core member 2 are configured such that end portions (1 to 10 μm) thereof as viewed in its radial direction are exposed from the core member 2. When the long fibers 16 are exposed in this manner, minute irregularities are generated on the surface of the core member 2, so that displacement between the core member 2 and the reinforcing fiber layer 3 can be suppressed.

In the fixture rod 1 according to one embodiment of the present disclosure, the fibers 4 of the core member 2 comprises the long fiber 16 and the short fiber 15. Although not illustrated, the fibers 4 of the core member 2 may comprise the short fiber 15 and the long fiber 16 described above, and have a part exposed from the surface of the core member 2 in the fixture rod 1 according to one embodiment of the present disclosure. When the short fibers 15 and the long fibers 16 are exposed in this manner, minute irregularities are generated on the surface of the core member 2, so that the displacement between the core member 2 and the reinforcing fiber layer 3 can be suppressed.

In the fixture rod 1 according to one embodiment of the present disclosure, the fiber 4 of the core member 2 is, for example, carbon, glass, aramid, boron, or SiC. Fibers other than these fibers can be used without being limited to specific fibers.

In the fixture rod 1 according to one embodiment of the present disclosure, the core member 2 contains a resin, and a thermosetting resin (for example, epoxy, phenol, unsaturated polyester, or the like) or a thermoplastic resin (for example, PA, PC, PPSU, POM, PP, PE, ABS, PS, PAEK, PEEK, or the like) can be used as the resin.

In the fixture rod 1 according to one embodiment of the present disclosure, the reinforcing fiber layer 3 is a fiber-reinforced resin, carbon, glass, boron, SiC, or aramid is used as a fiber, and a thermosetting resin (for example, epoxy, phenol, unsaturated polyester, or the like) or a thermoplastic resin (for example, PA, PC, PPSU, POM, PP, PE, ABS, PS, PAEK, PEEK, or the like) is used as a resin. With this configuration, it is possible to increase the bending rigidity and the strength of the reinforcing fiber layer.

It is configured such that the fixture rod 1 according to one embodiment of the present disclosure comprises a covering layer provided on the reinforcing fiber layer 3. The covering layer can be formed using, for example, epoxy, phenol, unsaturated polyester, PA, PC, PPSU, POM, PP, PE, ABS, PS, PAEK, or PEEK, but is not limited thereto.

Next, the core member 2 of the fixture rod 1 according to one embodiment of the present disclosure used for the spinal fixture 10 will be described with reference to FIGS. 5 to 8. In the fixture rod 1 according to one embodiment of the present disclosure, one or a plurality of recesses are formed on an outer surface of the core member 2. Here, the fiber 4 of the core member 2 is partially exposed from the outer surface of the core member 2 as described above, but may be exposed from a recess or may be exposed from other outer surfaces of the core member 2 (the same applies hereinafter). As a result, the contact surface area between the core member 2 and the reinforcing fiber layer 3 increases during molding, so that the bonding strength between the core member and the reinforcing fiber layer can be more significantly improved. This will be described more specifically below.

Figure 5:
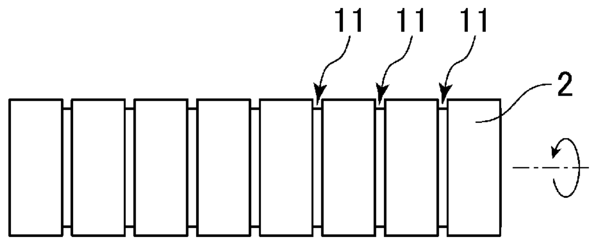
FIG. 5 is a view for describing a core member of the fixture rod according to one embodiment of the present disclosure.

As illustrated in FIG. 5, recesses (circumferential recesses) 11 are formed in a circumferential direction of the core member 2 having the partially exposed fiber 4 in the fixture rod 1 according to one embodiment of the present disclosure. Although seven recesses 11 are formed in the example illustrated in the drawing, any desired number of recesses can be provided, and the number is not limited to a specific number. Further, the recess 11 can be formed in the whole or a part of the core member 2 in the circumferential direction Alternatively, the recess 11 may be intermittently formed in the whole or a part of the core member 2 in the circumferential direction. When the recess is provided in the circumferential direction of the core member in this manner, the bonding area increases, and axial displacement between the core member 2 and the reinforcing fiber layer 3 can be suppressed.

Figure 6:
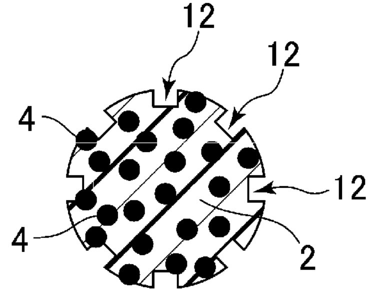
FIG. 6 is a view for describing a core member of the fixture rod according to one embodiment of the present disclosure.

Next, as illustrated in FIG. 6, recesses (axial recesses) 12 are formed in an axial direction of the core member 2 having the partially exposed fiber 4 in the fixture rod 1 according to one embodiment of the present disclosure. Although eight recesses 12 are formed in the example illustrated in the drawing, any desired number of recesses can be provided, and the number is not limited to a specific number. Further, the recess 12 can be formed in the whole or a part of the core member 2 in the axial direction Alternatively, the recess 12 may be intermittently formed in the whole or a part of the core member 2 in the axial direction. When the recess is provided in the axial direction of the core member in this manner, the bonding area increases, and rotational displacement between the core member 2 and the reinforcing fiber layer 3 can be suppressed.

Figure 7:
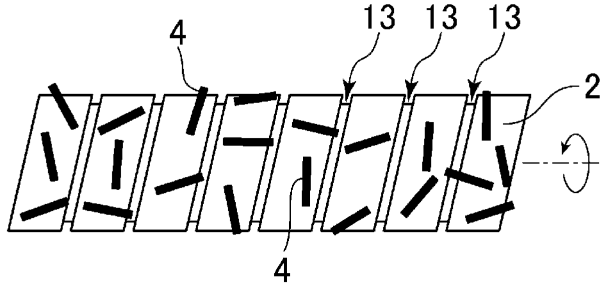
FIG. 7 is a view for describing a core member of the fixture rod according to one embodiment of the present disclosure.

Next, as illustrated in FIG. 7, recesses (inclined-direction recesses) 13 are formed so as to be inclined with respect to the circumferential direction of the core member 2 having the partially exposed fiber 4 in the fixture rod 1 according to one embodiment of the present disclosure. Although seven recesses 13 are formed in the example illustrated in the drawing, any desired number of recesses can be provided, and the number is not limited to a specific number. Further, the recess 13 can be formed on the whole or a part of the circumference of the core member 2. Alternatively, the recess 13 may be intermittently formed on the whole or a part of the circumference of the core member 2. As a result, when the recess is provided in a direction inclined with respect to the circumferential direction of the core member, the bonding area increases, and the axial displacement and rotational displacement between the core member 2 and the reinforcing fiber layer 3 can be suppressed.

Figure 8:
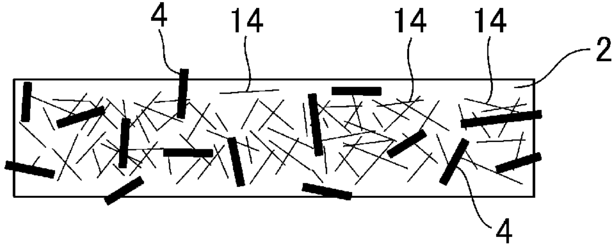
FIG. 8 is a view for describing a core member of the fixture rod according to one embodiment of the present disclosure.

Next, as illustrated in FIG. 8, recesses (different-direction recesses) 14 are formed on the surface of the core member 2 having the partially exposed fiber 4 so as to comprise two or more recesses formed in different directions in the fixture rod 1 according to one embodiment of the present disclosure. Although many recesses 14 are formed in the example illustrated in the drawing, any desired number of recesses can be provided, and the number is not limited to a specific number. Further, in a case where there are three or more recesses 14, two or more recesses 14 thereof may be formed in the same direction. Further, the recesses 14 can be formed on the whole or a part of the surface of the core member 2. Alternatively, the recess 11 may be intermittently formed on the whole or a part of the surface of the core member 2. As a result, when the recesses are provided in different directions in this manner, it is possible to suppress displacement in a plurality of different directions.

In the fixture rod according to one embodiment of the present disclosure, a depth of the recess is in a range of 3 μm to 200 μm. Accordingly, it is possible to set an appropriate range in which the displacement between the core member 2 and the reinforcing fiber layer 3 is suppressed while suppressing a change and a variation in the rigidity due to the recess.

The spinal fixture 10 according to one embodiment of the present disclosure comprises any of the fixture rods 1 described above. As a result, it is possible to provide the fixture rod having the significantly improved bonding force between the core member and the reinforcing fiber layer, high rigidity, and high durability against the deformation load, and the spinal fixture comprising the same.

Figure 9A:
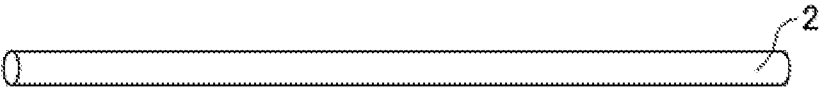
FIG. 9A is a view for describing a method for molding the fixture rod according to one embodiment of the present disclosure.
Figure 9B:
FIG. 9*b* is a view for describing a method for molding the fixture rod according to one embodiment of the present invention.
Figure 9C:
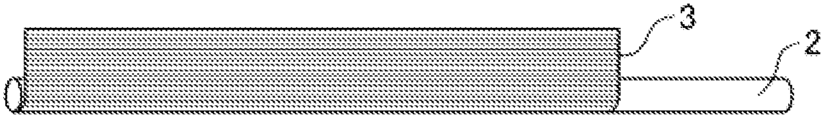
FIG. 9*c* is a view for describing a method for molding the fixture rod according to one embodiment of the present invention.

Next, a method for manufacturing the fixture rod 1 according to one embodiment of the present disclosure will be described with reference to FIG. 9. First, as Step 1, a core member (also referred to as a core material) (comprising each of modes in FIGS. 3 to 8 described above) is prepared (FIG. 9*a*). Next, as Step 2, a fiber-reinforced resin material is prepared (FIG. 9*b*). Next, as Step 3, the fiber-reinforced resin material is wound around the core member to form a fiber-reinforced resin material integrated member (FIG. 9*c*).

Figure 9D:
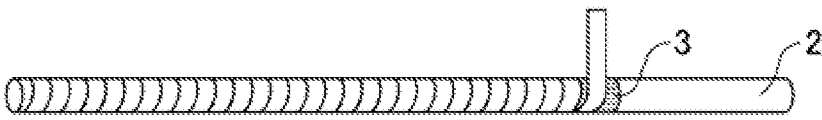
FIG. 9*d* is a view for describing a method for molding the fixture rod according to one embodiment of the present invention.
Figure 9E:
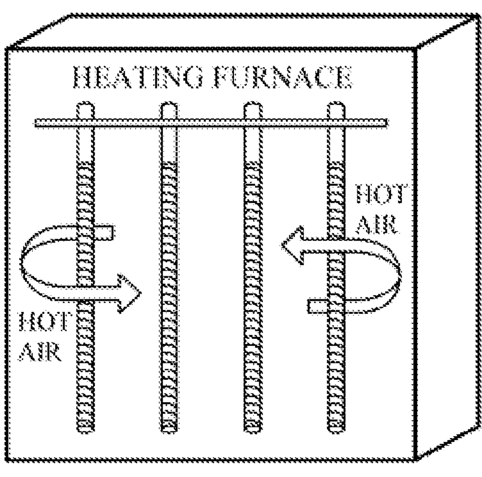
FIG. 9*e* is a view for describing a method for molding the fixture rod according to one embodiment of the present invention.
Figure 9F:
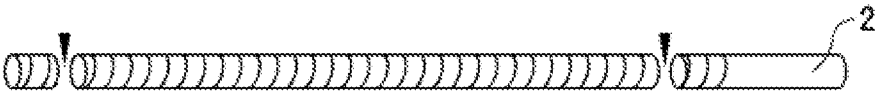
FIG. 9*f* is a view for describing a method for molding the fixture rod according to one embodiment of the present invention.
Figure 9G:
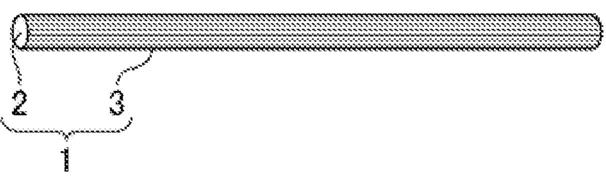
FIG. 9*g* is a view for describing a method for molding the fixture rod according to one embodiment of the present invention.

Next, in Step 4, a tape is wound around an outer surface of a fiber-reinforced resin material integrated member as an outer die (FIG. 9*d*). Next, in Step 5, the fiber-reinforced resin material integrated member around which the tape is wound is fired (molded) (FIG. 9*e*). Thereafter, as Step 6, the fiber-reinforced resin material integrated member after firing is taken out, and an unnecessary portion is cut (FIG. 9*f*). Finally, as Step 7, the tape of the fiber-reinforced resin material integrated member from which the unnecessary portion has been cut is removed, whereby the fixture rod 1 according to one embodiment of the present disclosure comprising the core member and a fiber-reinforced resin layer can be obtained (FIG. 9*g*).

With the fixture rod 1 according to one embodiment of the present disclosure formed in this manner, it is possible to provide the fixture rod having significantly improved bonding strength between the core member and a reinforcing fiber layer, high rigidity, and high durability against a deformation load. More specifically, as the fiber of a heartwood is exposed and inserted into the reinforcing fiber layer, bonding between the core member and the reinforcing fiber layer is strengthened. Further, a solid double structure is adopted, and a material having a large average bending elastic modulus is used for an outer layer as will be described later, and thus, it is possible to provide the fixture rod having excellent bending rigidity and crushing strength of the entire rod. Here, the average bending elastic modulus refers to a value calculated by dividing the bending rigidity of the entire corresponding portion by a second moment of the corresponding portion.

Dimensions, materials, and arrangements of the components described in this specification are not limited to those explicitly described in the embodiments, and the components may be modified to have any dimensions, materials, and arrangements that may fall within the scope of the present disclosure. Further, components not explicitly described herein can be added to the described embodiments, or some of the components described in each embodiment can be omitted.

REFERENCE SIGNS LIST

- 1 Fixture rod
- 2 Core member
- 3 Reinforcing fiber layer
- 4 Fiber
- 10 Spinal fixture
- 11 Recess (circumferential recess)
- 12 Recess (axial recess)
- 13 Recess (inclined-direction recess)
- 14 Recesses (different-direction recesses)
- 15 Fiber (short fiber)
- 16 Fiber (long fiber)
- 18 Screw member
- 20 Rod fixing member
- 21 Recess
- 22 Pressing member

The invention claimed is:

1. A fixture rod comprising:

a core member containing fibers and having one elongate recess or a plurality of elongate recesses formed on an outer surface of the core member, a depth of the one recess or each of the plurality of recesses is in a range of from 3 μm to 200 μm; and a reinforcing fiber layer provided on the core member, the reinforcing fiber layer covering the one elongate recess or the plurality of elongate recesses, the fibers of the core member comprise long fibers, and a portion of the long fibers each have an end portion that is exposed from a radially facing surface of the core member and have a part that is embedded in the reinforcing fiber layer.

2. The fixture rod according to claim 1, wherein the fibers of the core member further comprise short fibers.

3. The fixture rod according to claim 1, wherein the fibers of the core member further comprise fibers whose end portion are exposed from a longitudinally facing surface of the core member.

4. The fixture rod according to claim 1, wherein the fibers of the core member are carbon, glass, aramid, boron, or SiC.

5. The fixture rod according to claim 1, wherein the one elongate recess or the plurality of elongate recesses have a longest dimension that extends in a circumferential direction of the core member.

6. The fixture rod according to claim 1, wherein the one elongate recess or the plurality of elongate recesses have a longest dimension that extends in an axial direction of the core member.

7. The fixture rod according to claim 1, wherein the one elongate recess or the plurality of elongate recesses have a longest dimension that extends in a direction inclined with respect to a circumferential direction of the core member.

8. The fixture rod according to claim 1, wherein the core member comprises the plurality of elongate recesses, and two or more slongate recesses of the plurality of elongate recesses have a longest dimension that extends in different directions.

9. The fixture rod according to claim 1, wherein the core member contains a resin, and the resin being any of epoxy, phenol, unsaturated polyester, PA, PC, PPSU, POM, PP, PE, ABS, PS, PAEK, or PEEK.

10. The fixture rod according to claim 1, wherein the reinforcing fiber layer contacts and is bonded to the outer surface of the core member where the one elongate recess or the plurality of elongate recesses are formed.

11. A spinal fixture that is configured to be fixed to a spine and comprises the fixture rod according to claim 1 and a screw.

* * * * *